United States Patent [19]

Martin

[11] Patent Number: 4,561,104
[45] Date of Patent: Dec. 24, 1985

[54] AUTOMATED INSPECTION OF HOT STEEL SLABS

[75] Inventor: Ronald J. Martin, Burnsville, Minn.

[73] Assignee: Honeywell Inc., Minneapolis, Minn.

[21] Appl. No.: 571,220

[22] Filed: Jan. 16, 1984

[51] Int. Cl.⁴ .............................................. G06K 9/56
[52] U.S. Cl. ........................................ 382/8; 356/237; 358/93; 358/100; 358/101; 358/106; 382/22; 382/50
[58] Field of Search ................ 358/93, 100, 101, 106, 358/107; 382/1, 8, 22, 54, 50; 356/237; 250/562–563, 571–572, 330–334; 364/507

[56] References Cited

U.S. PATENT DOCUMENTS

| | | | |
|---|---|---|---|
| 4,118,732 | 10/1978 | Ichijima et al. | 358/106 |
| 4,131,490 | 12/1978 | Oishi et al. | 358/10 |
| 4,207,593 | 6/1980 | Deutsch et al. | 358/106 |
| 4,223,346 | 9/1980 | Neiheisel et al. | 358/106 |
| 4,253,768 | 3/1981 | Yaroshuk et al. | 356/431 |
| 4,319,270 | 3/1982 | Kimura et al. | 358/100 |
| 4,428,672 | 1/1984 | Allard et al. | 250/358.1 |

OTHER PUBLICATIONS

Baier et al, "Edge Analysis in Digitized Grey Level Patterns", *IBM Tech. Disclosure Bulletin*, vol. 25, No. 6, Nov. 1982.

*Primary Examiner*—Leo H. Boudreau
*Attorney, Agent, or Firm*—Charles G. Mersereau

[57] ABSTRACT

The disclosure relates to a real time digital image enhancement system for performing the image enhancement segmentation processing required for a real time automated system for detecting and classifying surface imperfections in hot steel slabs. The system provides for simultaneous execution of edge detection processing and intensity threshold processing in parallel on the same image data produced by a sensor device such as a scanning camera. The results of each process are utilized to validate the results of the other process and a resulting image is generated that contains only corresponding segmentation that is produced by both processes.

7 Claims, 5 Drawing Figures

AUTOMATED INSPECTION OF HOT STEEL SLABS

The Government of the United States of America has rights in this invention pursuant to Contract No. DE-FC07-79CS40242 awarded by the U.S. Department of Energy.

BACKGROUND OF THE INVENTION

Reference to Previous Application

The present invention is an improvement over an invention disclosed in a patent application entitled Real Time Automated Inspection, Ser. No. 374,373 filed May 3, 1982, now U.S. Pat. No. 4,519,041 issued May 21, 1985 and assigned to the same assignee as the present invention. The disclosure of that application is deemed to be incorporated herein by reference to the extent necessary.

The invention relates generally to a real time digital image enhancement system and, more particularly, to an improved method for performing the image enhancement segmentation processing required for a real time automated system for detecting and classifying surface imperfections in objects such as hot steel slabs.

The American steel industry is one of the largest consumers of energy in the United States. The trend in steelmaking technology in the United States is toward the continuous casting of steel. In a continuous caster, molten steel is continuously poured into a mold which is water cooled. The steel as it solidifies is drawn out of the mold in a perpetual ribbon on a roll table and is cut to form slabs. The steel slabs often have surface imperfections or defects which must be detected and evaluated prior to further processing of the slabs. In most steel mills the hot slab coming out of a caster is cooled to facilitate human inspection for surface defects and imperfections. If the surface imperfections are found to be sufficiently serious to make it necessary to condition a slab before continuing with the processing, as by machining, for example, the slab is routed to a processing area where such conditioning is performed.

If, on the other hand, the surface imperfections are minor or not serious such that intermediate conditioning is not required, the slab is reheated for further processing. Thus, if it were known beforehand that intermediate conditioning was not required, the substantial cost of reheating the slab for further processing could be saved.

An automated inspection system capable of inspecting a slab coming out of the caster while it is still hot avoids the intermediate cooling and reheating process currently necessary for manual inspection and thus eliminates the waste of energy associated therewith in those cases where the surface imperfections intermediate conditioning is not necessary.

The concept of an automatic inspection system involves a data collection camera which views the steel slab moving in a transverse direction relative to the scan line of the camera. The data camera, which has picture sensing elements, collects data and the data in the form of digital values is then routed via interface electronics to the digital image enhancement processing stage.

Image enhancement entails several operations that improve the appearance of an image to a human viewer, or operations to convert an image to a format better suited to machine processing, but still recognizable as an image.

Segmentation processing as it applies to image processing is the process of enhancing or segmenting out objects or features of interest from an image. The two primary forms of segmentation processing are edge detection and intensity region thresholding based processes.

Image edges are places within an image where there are relatively abrupt changes in the intensity level. There are existing algorithmic operators such as the Roberts edge operator which are used for edge detection within image frames. The operator requires computations on every picture element or pixel within the image to determine the edge value of each pixel. The edge value computed is compafed to a threshold value to determine if it may be considered an edge within the image.

Likewise, it is possible to compare each picture element or pixel gray scale value to a gray scale threshold and extract areas of uniform gray scale from an image. This later form of image segmentation is called gray scale or intensity region thresholding, and also requires computation on each picture element or pixel within an image.

Existing real time digital image processing systems employ only one type of segmentation process, edge or intensity thresholding due to the severe time constraints of real time digital image processing.

SUMMARY OF THE INVENTION

The concept of the invention is to provide a unique digital process that provides simultaneous edge detection processing and intensity threshold processing to be executed in parallel on the same image data. This process improves the throughput performance and detection performance of a real time digital image processing system.

The digital image enhancement processing system disclosed in the above-referenced patent application involves only an edge segmentation algorithm which performs edge segmentation on the data collected by the camera and utilizes the Roberts gradient edge operator for that function.

Because steel slab imperfections are mostly linear discontinuities, edge segmentation algorithms are useful as in image enhancement technique. The Roberts gradient edge operator is one particular edge segmentation technique that is well suited to image enhancement for real time systems due to the simplistic nature of computations required for the operator. The technique does, however, require computations on every picture element or pixel within the total image sampled to determine the edge value of each pixel. The edge value computed is then compared to an edge value threshold in order to determine whether it should be considered to be an edge within the image.

A problem relative to edge segmentation is that the background surface on the steel slab or other object may not be uniform and may contain areas of surface discontinuities that are not true imperfections but may appear as imperfections to an edge gradient operator. The normal edge enhancement process may thus provide a greater imperfection or crack portrayal segmentation than actually exists and thereby, in some cases, give a false indication of a need for intermediate conditioning.

The present invention provides a process which retains the advantages of the edge segmentation process but avoids the disadvantages thereof. This concept is implemented by utilizing the edge segmentation process in parallel with an intensity level process and in effect to use the results of each process to validate the results of the other process.

The intensity level process involves comparing each picture element gray scale value to a threshold. Those values that are above or below the threshold can be extracted and regions of uniform gray scale can be determined from an image. This type of image segmentation is called intensity region thresholding.

Figure 1:
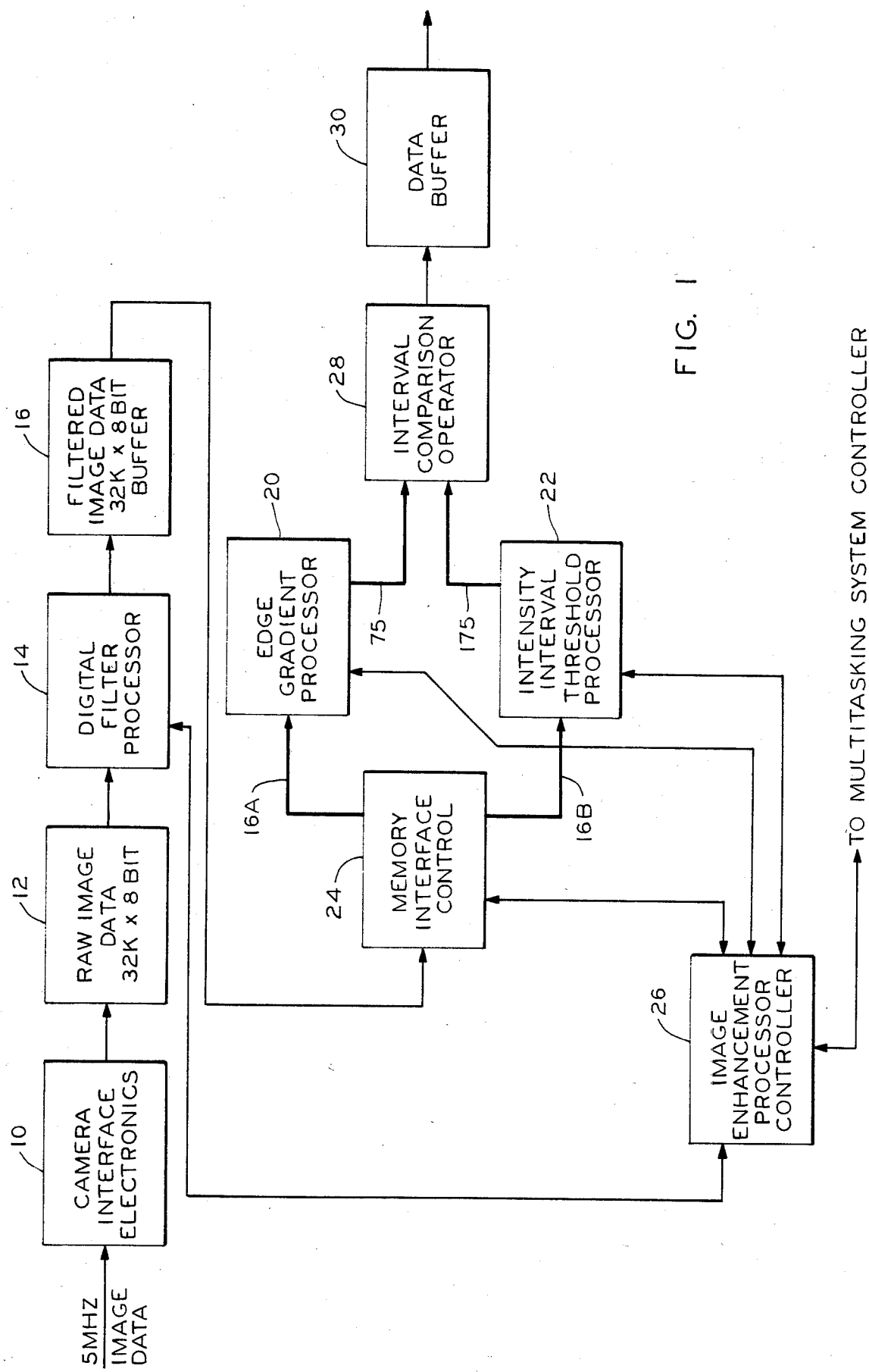
FIG. 1 is a block diagram of an image enhancement processor (IEP) which processes image data from a camera sensor system and embodies the dual segmentation processing stage in accordance with the invention.

The image enhancement processor shown in FIG. 1 executes arithmetic functions on image data consisting of input from a sensor system and passes the processed data, which will consist of image intervals of interest, to a classification system. The IEP comprises a data memory for storage of image data, a digital filter for filtering the image data, and two parallel operating subprocessors for executing the edge operator algorithm and the interval threshold algorithm. The IEP will also have a sequence controller that has the function of interfacing the IEP classification systems and also for controlling the sequencing of the internal functions of the digital filter and edge and intensity processors, and all internal memory control.

In the image enhancement processor shown in FIG. 1, the image data sensed by a data collecting camera is directed from a camera interface 10 through the labeled processing stages 12 and 14 to the buffer 16. Digital filtering and sensor compensation performed in the stages 12 and 14 ensure that uniform pixel intensity data is present in the buffer 16. Dual segmentation processing stages 20 and 22 receive data from the buffer 16 via buses 16A and 16B under the control of a memory interface control 24.

Figure 2:
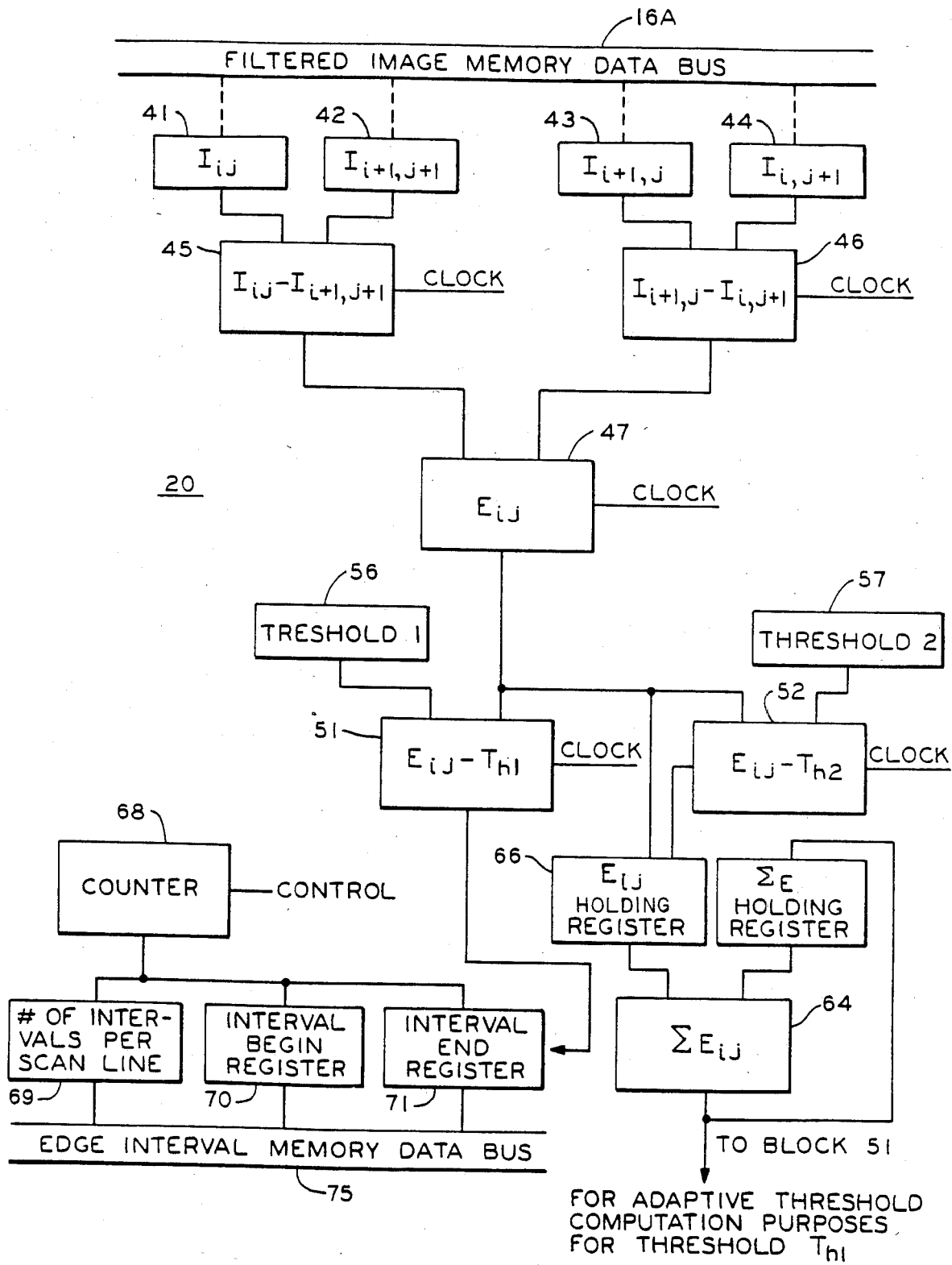
FIGS. 2 and 3 are block diagrams, respectively, of an edge gradient operator processor and an intensity interval operator, both processors being parts of the image enhancement processor of FIG. 1.
Figure 3:
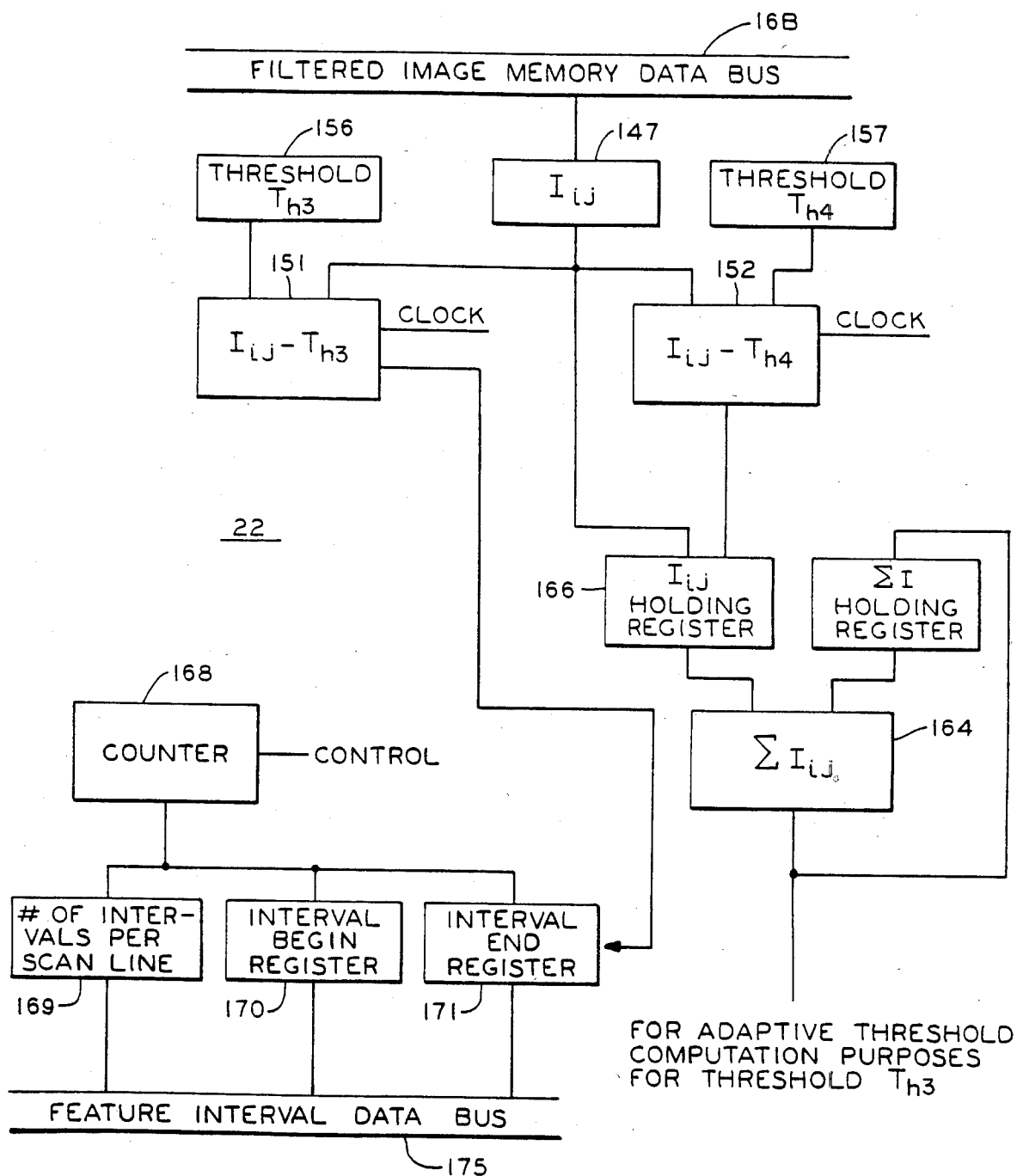

FIGS. 2 and 3 are block diagrams of the dual segmentation stages 20 and 22 of the IEP. A function controller 26 (FIG. 1) provides the timing and control logic required by the interval operator processors 20 and 22 in addition to providing all interface control for the IEP and the external IEP systems.

After thresholding operations performed by the processors 20 and 22, each scan line of the image will contain segments of the image corresponding to the objects of interest which in this instance are the slab imperfections. These segments are referred to as intervals on any scan line of the image.

Interval comparisons from the two processors 20 and 22 are performed in a processor 28 (FIG. 1) with an interval comparison operator. The resulting combined interval based on overlapping edge and intensity intervals is directed to a data buffer 30.

The IEP data throughput requirement during the edge gradient operation and intensity threshold operation is on the order of 10 million operations per second. The interval operator processors 20 and 22 receive image intensity data from the image data buffer 16 and respectively generate "object of interest" intervals based on Roberts edge thresholds and intensity thresholds. Image intensity data from buffer 16 is referenced for each intensity pixel. Each pixel is used simultaneously by each of the processors 20 and 22 in order to minimize data accessed from the buffer 16 for the same image intensity pixel since both image operator processors can run simultaneously. Pipelining the image data in parallel through the interval operators of processors 20 and 22 permits the computations on each scan line to be made within the allowed computation time for each scan line. The edge gradient operator processor 20 utilizes the following Roberts gradient operator:

$$E_{ij} = [I(i,j) - I(i+1, j+1)] = [I(i+1, j) - I(i, j+1)]$$

The edge value $E_{ij}$ computed for each intensity pixel $I_{ij}$ can be compared to an edge value threshold $T_e$. If $E_{ij}$ is greater than or equal to the edge threshold $T_e$ then the operator processor saves the current pixel counter in a holding register as either the beginning or the ending of an edge interval.

FIGS. 2 and 3 respectively disclose the block diagrams for the edge gradient operator and the intensity interval operator of the processors 20 and 22. In these figures the "i" denotes the current image data scan line being processed and the "j" denotes the individual pixel number on each scan line of image data. In the edge gradient operator 20 of FIG. 2, four pixel intensities 41 to 44 from filtered image memory data bus 16A are required as indicated to compute the Roberts edge gradient $E_{ij}$ (block 47) from two adjacent scan lines. Once the first four image intensities values 41 to 44 have been accessed, only two new intensities need be accessed to compute the edge value for each "next" computation for the $E_{ij}$ values for the remainder of the scan line. When the computations are completed in blocks 45 and 46 for each $E_{ij}$ value (block 47), it is compared in blocks 51 and 52 to two gray scale thresholds Th$_1$ and Th$_2$ indicated in blocks 56 and 57. Threshold Th$_1$ is a threshold used to determine if each $E_{ij}$ value is the beginning or ending of an edge interval. Threshold Th$_2$ is a threshold used to determine if the computed $E_{ij}$ value is to be used in the computation of the adaptive threshold Th$_1$.

The threshold Th$_1$ is computed by the following method:

$$Th_1 = \frac{1}{N} \cdot \sum^{N} E_{ij}$$

The threshold Th$_1$ is actually an average value over each scan line. This implies that for edge intervals to be created, the computed value $E_{ij}$ must be above the average value for the preceding scan line. An $E_{ij}$ adder/shifter 64 is used to sum the computed values of $E_{ij}$ for each scan line. The summed valued is then shifted for the correct division.

In operation, the comparison in box 52 utilizes the threshold Th$_2$ which is a minimum value for qualifying the validity of an $E_{ij}$ value. If the $E_{ij}$ value is less than the Th$_2$ value it is not used in computing the Th$_1$ value.

The $E_{ij}$ value tested is held in a holding register 66 during the test in box 52 and is passed to the adder/shifter 64 only if enabled by a positive result in box 52. The edge gradient operator processor 20 also has a counter 68 and a register 69 which counts for each "j" value or pixel increment along each scan line. When a comparison of $E_{ij}$ and threshold $Th_1$ in box 51 results in a beginning or ending value for an edge interval, the pixel counter value will be shifted into temporary "interval begin" and "interval end" holding registers 70 and 71 which will then be moved to the edge interval memory buffer 75.

FIG. 3 is a block diagram of the intensity interval operator processor 22. The structure of the operator processor 22 is similar to that of the edge gradient operator processor 20. For each pixel intensity value $I_{ij}$, where "i" denotes the ith particular scan line and "j" denotes each jth pixel value along each scan line, the $I_{ij}$ pixel is compared to two thresholds $Th_3$ and $Th_4$. These thresholds have different numerical values than the thresholds of the edge threshold processor 20 but are identical functionally.

The pixel intensity 147 from the filtered memory data bus 16B is compared with thresholds $Th_3$ and $Th_4$ (blocks 156 and 157). The computations are made in blocks 151 and 152.

The threshold $Th_3$ is used to determine if the individual pixel intensity $I_{ij}$ is the beginning or end of an intensity region or interval of interest. The threshold $Th_4$ is used to determine if the pixel intensity value is to be used in the computation of the adaptive threshold $Th_3$. The threshold $Th_3$ is computed using the following method:

$$Th_3 = \frac{1}{N} \sum^N I_{ij}.$$

N is the number of pixel intensities for each scan line. Thus, in this method the thresholding $Th_3$ is actually an average intensity level for the preceding scan line. An $I_{ij}$ adder/shifter 164 is used to sum the computed values of $I_{ij}$ for each scan line. The summed value is then shifted for the correct division.

In operation, the comparison in box 152 utilizes the threshold $Th_4$ which is a minimum value for qualifying the validity of an $I_{ij}$ value. If $I_{ij}$ the value is less than the $Th_4$ value it is not used in computing the $Th_3$ value. The $I_{ij}$ value tested is held in a holding register 166 during the test in box 152 and is passed to the adder/shifter 164 only if enabled by a positive result in box 152.

In a manner identical to the edge gradient operator 20, a pixel counter 168 and register 160 are utilized to keep track of the current pixel location along the scan line. When an individual pixel intensity $I_{ij}$ exceeds the threshold $Th_3$, the counter's value is shifted into a holding region 170 or 171 depending on whether the pixel intensity $I_{ij}$ is the beginning or ending value for an intensity region of interest. From the registers 169, 170 and 171 the data thereof is moved to the interval memory buffer 175. The function of the interval comparison operation is to make comparisons between the intervals of interest generated by the edge gradient operator and the intensity interval operator.

Figure 4:
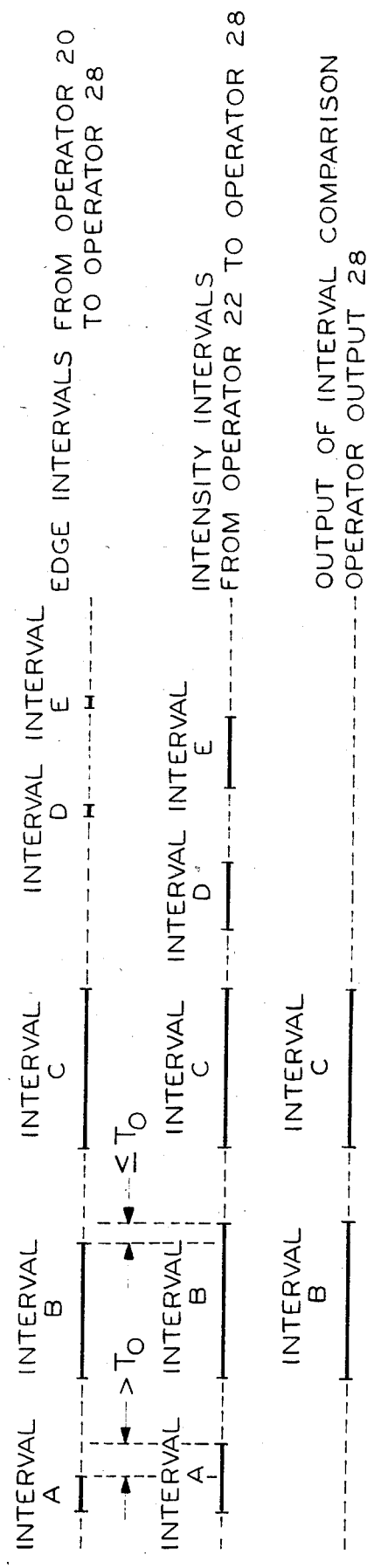
FIG. 4 shows hypothetical cases for processing intervals generated by the processors of FIGS. 2 and 3.

FIG. 4 shows hypothetical cases for intervals generated by the edge gradient operator 20 and the intensity operator 22 for the same image scan line. In order for the interval to be generated by the interval comparison operator 28, intervals generated by the edge and intensity operators must overlap, that is, they must exist over the same region on the scan line. There is a tolerance or threshold allowable for the overlap between the two intervals being compared. Therefore, an interval overlap threshold "$T_o$" is used in the computation for combined interval generation in the following method:
(Edge Interval Begin-Intensity Interval Begin) $T_o$ and
(Edge Interval End-Intensity Interval End) $T_o$ If the respective begin or end interval value is less than or equal to the overlap threshold $T_o$, then a combined interval value Interval Begin or Interval End will be formed and the corresponding values will be placed in the combined intervals memory data buffer 30.

FIG. 4 depicts this concept. For the interval comparison A, the difference in the corresponding ending values for the intervals is greater than the interval overlap threshold $T_o$ and there is no resultant output from the operation 28. For the interval comparison B the edge and intensity intervals are within the allowable interval overlap $T_o$ and there is a resultant output from operator 28.

Figure 5:
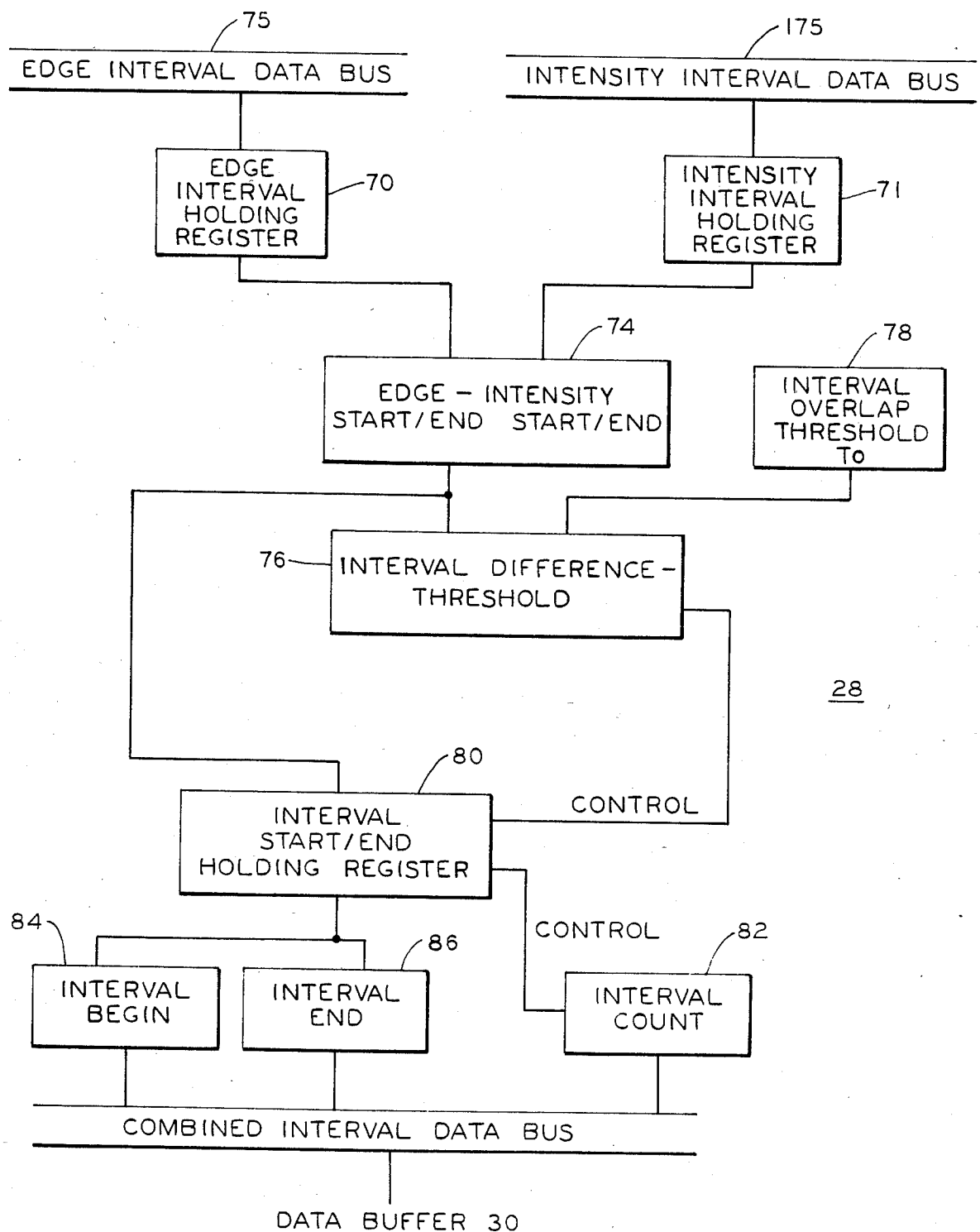
FIG. 5 shows an interval comparison processor which processes the outputs of the processors of FIGS. 2 and 3 in accordance with the concept illustrated in FIG. 4.

FIG. 5 is a block diagram of the interval comparison operation operator 28. edge and intensity interval beginning and end points from buses 75 and 175 are placed in holding registers 70 and 71. The begin and end point differences are computed in a process 74 and those values are then compared in block 76 to the interval overlays threshold $T_o$ (block 78) discussed above. If the difference between the interval difference is less than the interval overlays threshold $T_o$, the respective beginning or ending value of the interval is placed in the combined interval begin or end register 80. The interval count in register 82 is incremented and the interval/begin data is stored in "interval begin" and "interval end" registers 84 and 86. The interval begin/end data and number of intervals is then stored in the combined interval data memory 30.

The image enhancement processor (FIG. 1) also contains a control processor (not shown) which provides all necessary timing command and control signals for the edge gradient operator 20, the intensity interval operator 22 and the interval comparison operator 28. In addition, external interface control and memory and data bus control signals will be provided by the IEP control processor. Implementation of the IEP can be done using several separate digital electronic boards interconnected using a memory data and control signal bus.

The embodiments of the invention in which an exclusive property or right is claimed are defined as follows:

1. A method for the real time enhancement of an image to provide for detection and classification of characteristic type surface imperfections occurring on the surface of a material of interest, comprising the steps of; forming a single digital image of said surface having digital values, processing said digital image to simultaneously perform, on the fly and in parallel, edge enhancement and intensity interval extraction of said digital image to respectively form edge and intensity enhanced intervals; and simultaneously comparing said edge and intensity enhanced intervals to generate image enhanced intervals which correspond to the joint existence of edge intervals and intensity intervals.

2. A method for the real time enhancement of an image to provide for detection and classification of characteristic type surface imperfections occurring on the surface of a material of interest, comprising the steps of; forming a single digital image of said surface having digital values, processing said digital image to simultaneously perform, on the fly and in parallel, edge enhancement and intensity interval extraction of said digital image, said edge enhancement being performed with an edge enhancement operator to form an edge enhanced image containing intervals of said image corresponding to the edges of surface imperfections, said intensity interval extraction being performed with an image intensity enhancement operator to form image intensity intervals of said image corresponding to the intensity of areas of surface imperfections; and simultaneously comparing said edge and intensity enhanced intervals to generate image enhanced intervals which correspond to the joint existence of edge intervals and intensity intervals.

3. A method according to claim 2 wherein said edge enhancement operator is a Roberts gradient edge operator.

4. A method according to claim 2 wherein said edge and intensity intervals are each derived with first and second thresholds, said first threshold being an average pixel value over each scan line used to determine if each computed pixel value indicates the beginning or ending of an interval, said second threshold being a minimum pixel value for qualifying the use of pixel values in computing said first threshold value.

5. A method according to claim 1 wherein said comparison of edge and intensity enhanced intervals determines the existence of overlap of corresponding intervals and allows predetermined interval beginning and ending tolerances in the generating of said image enhanced intervals.

6. A system for the real time enhancement of an image to provide for detection and classification of characteristic type surface imperfections occurring on the surface of a material of interest, comprising; means for forming a single digital image of said surface having digital values, means for proccessing said digital image to simultaneously perform, on the fly and in parallel, edge enhancement and intensity interval extraction of said digital image to respectively form edge and intensity enhanced intervals, and means for simultaneously comparing said edge and intensity enhanced intervals and generating image enhanced intervals which correspond to the joint existence of edge intervals and intensity intervals.

7. A system for the real time enhancement of an image to provide for detection and classification of characteristic type surface imperfections occurring on the surface of a material of interest, comprising, the for forming a single digital image of said surface having digital values, means for processing said digital image to simultaneously perform, on the fly and in parallel, edge enhancement and intensity interval extraction of said digital image, an edge enhancement operator for performing to form said edge enchancement an edge enhanced image containing intervals of said image corresponding to the edges of said surface imperfections, an image intensity enhancement operator for performing said intensity interval extraction to form image intensity intervals of said image corresponding to the intensity of areas of surface imperfections, and means for simultaneously comparing said edge and intensity enhanced intervals and generating image enhanced intervals which correspond to the joint existence of edge intervals and intensity intervals.

* * * * *

UNITED STATES PATENT AND TRADEMARK OFFICE
CERTIFICATE OF CORRECTION

PATENT NO. : 4,561,104
DATED : Dec. 24, 1985
INVENTOR(S) : RONALD J. MARTIN

It is certified that error appears in the above-identified patent and that said Letters Patent is hereby corrected as shown below:

Column 8, line 24, after "performing" delete "to form";

line 24, cancel "enchancement" and substitute

--enhancement--;

line 24, after "enhancement" insert --to form--.

Signed and Sealed this

Fifteenth Day of April 1986

[SEAL]

Attest:

DONALD J. QUIGG

Attesting Officer

Commissioner of Patents and Trademarks